United States Patent [19]

Domb

[11] Patent Number: 5,498,729

[45] Date of Patent: Mar. 12, 1996

[54] PRODRUG COMPOSITIONS

[76] Inventor: Abraham J. Domb, 16 Gogdol Eder Street, Efrat 90435, Israel

[21] Appl. No.: 20,168

[22] Filed: Feb. 22, 1993

Related U.S. Application Data

[63] Continuation of Ser. No. 456,376, Dec. 26, 1989, abandoned.

[51] Int. Cl.$^6$ .................................................. C07D 209/26
[52] U.S. Cl. ..................... 548/500; 546/272; 546/281; 546/341; 548/536; 560/143; 562/887
[58] Field of Search ..................... 548/500, 536; 546/272, 281, 341; 560/143; 562/887

[56] References Cited

U.S. PATENT DOCUMENTS

| | | | |
|---|---|---|---|
| 2,236,125 | 3/1941 | Wiezevich | 260/341 |
| 2,423,569 | 7/1947 | Sokol | 260/479 |
| 2,577,699 | 9/1949 | Cooper | 260/239.1 |
| 3,763,152 | 10/1973 | Wolf et al. | 260/243 C |
| 3,875,224 | 4/1975 | Finkbeiner et al. | 260/537 R |
| 4,757,128 | 7/1988 | Domb et al. | 528/271 |
| 4,789,724 | 12/1988 | Domb et al. | 527/176 |
| 4,851,426 | 7/1989 | Ladkani et al. | 548/500 |
| 4,857,311 | 8/1989 | Domb et al. | 428/78 |
| 4,863,965 | 9/1989 | Jansen et al. | 514/576 |
| 4,868,201 | 9/1989 | Fukaya et al. | 548/500 |
| 4,888,176 | 12/1989 | Langer et al. | 424/426 |

FOREIGN PATENT DOCUMENTS

| | | |
|---|---|---|
| 738726 | 2/1980 | Belgium . |
| 1002036 | 12/1976 | Canada . |
| 2126037 | 12/1971 | Germany . |
| 1069775 | 5/1967 | United Kingdom . |
| 1175933 | 1/1970 | United Kingdom ............... 548/500 |
| WO87/02891 | 5/1987 | WIPO . |

OTHER PUBLICATIONS

Leong, K. W., "Bioerodible Polyanhydrides as Drug–Carrier Matrices, I: Characterization, Degradation and Release Characteristics," *J. Biomed. Mat. Res.*, vol. 19, 941–955 (1985).

Leong, K. W., et al., "Bioerodible Polyanhydrides as Drug–Carrier Matrices, II: Biocompatibility and Chemical Reactivity," *J. Biomed. Mat. Res.*, vol. 20, 51–64 (1986).

Kydonieus, A. F., *Controlled Release Technologies*, CRC Press, Inc., Boca Raton, Florida (1977).

Harrison, I. T., et al., *Nonsteroidal Antiinflammatory Agents*, (1970).

Child, R. G., et al., *Journal of Pharmaceutical Sciences*, 66(4) (1977).

Tocoo, D. J., et al., *Drug Metabolism and Disposition*, 10(1) (1982).

Tipnis, V., et al., *Journal of Chromatography*, 345, 396–401 (1985).

I. T. Harrison, et al., "Nonsteroidal Antiinflammatory Agents 6–Substituted 2–Naphthylacetic Acids", *J. Med. Chem.* 13, 203–205 (1970).

R. G. Child, et al., "Fenbufen, a New Anti–Inflammatory Analgesic: Synthesis and Structure–Activity Relationships of Analogs", *J. Pharm. Sci.* 66(4), 466–476 (1977).

D. J. Tocco, et al., "The Physiological Disposition and Metabolism of Enalapril Maleate in Laboratory Animals", *Drug Metab. Disp.* 10(1), 15–19 (1982).

V. Tipnis, et al., "Determination of pentopril, an angiotensin converting enzyme inhibitor, and its active metabolite in urine", *J. Chromatog.* 345, 396–401 (1985).

*Primary Examiner*—David B. Springer
*Attorney, Agent, or Firm*—Patrea L. Pabst

[57] ABSTRACT

Compositions degrading by hydrolysis to release a bioactive compound having carboxylic acid moieties, which are organic acid anhydrides having the following formula:

Formula 1:

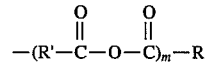

wherein R' is a residue of a therapeutic bioactive compound, for example, a non-steroidal anti-inflammatory agent; a penicillin or cephalosporin antibiotic; or bioactive compounds for non-therapeutic use, for example, herbicides, insecticides, fungicides, antimicrobials, pesticides, pheromones, and fertilizers; m is an integer of between 1 and 3; and R is a carrier. The resulting mixed anhydrides are characterized by having between one and three drug molecules attached to a single carrier molecule. The prodrugs are highly susceptibility to hydrolytic degradation in a predictable and controlled fashion, have variable solubilities in water and lipids, with increased biomembrane transport, elicit a bio-affecting/pharmacological response, and are less irritating to topical and gastric or intestinal mucosal membranes.

11 Claims, No Drawings

PRODRUG COMPOSITIONS

This application is a continuation of 07/456,376, filed Dec. 26, 1989, now abandoned.

BACKGROUND OF THE INVENTION

The present invention relates to novel and useful derivatives of biologically active agents containing a carboxylic acid function.

A wide variety of compounds containing carboxylic acid functions are biologically active. Examples include the non-steroidal anti-inflammatory agents such as naproxen, indomethacin, and voltaren; penicillin and cephalosporin antibiotics such as ampicillin and cefmetazole; herbicides such as Tordon, Endothal, and Amiben; as well as other compounds having biological properties.

The unionized form of a drug is, in general, absorbed more efficiently than its ionic species since the carboxylic acid group is significantly ionized at physiological pH, the result is that agents with carboxylic acid moieties are poorly absorbed through lipid-water membrane barriers. In addition, some acidic drugs, such as the non-steroidal anti-inflammatory agents aspirin, naproxen, ibuprofen, and indomethacin, are irritating to the mucous membrane of the gastrointestinal tract. The general approach to solve these problems has been to esterifying the carboxylic acid function to produce lipophilic and non-irritating prodrug forms, provided that the parent bioactive agent can be released from the esterified form with activity (Design of Prodrugs, H. Bundgaard editor, Elselvier, New York 1985). However, several aliphatic or aromatic esters of carboxylic acid drugs are not sufficiently labile in vivo to ensure a sufficiently high rate and extent of conversion from the esterified form. For example, ethyl esters of naproxen (Harison, I. T. et al. *J. Med. Chem.*, 13, 203, 1970) and fenbufen (Child, R .G. et al. *J. Pharm. Sci.*, 66, 466, 1977) have lower anti-inflammatory activity relative to the free acids which was attributed to the resistance of the esters to be hydrolyzed in vivo.

In contrast, ethyl ester derivatives of angiotensin-converting enzyme inhibitors have improved oral bioavailability. Enalapril is a clinically used ethyl ester prodrug of enalaprillic acid. Plasma enzymes do not hydrolyze the esters and the necessary conversion of the ester to the free acid predominantly takes place in the liver (Tocco, D. J. et al., *Drug Metab. Disp.* 10, 15, 1982). Accordingly, liver function may be a very important requirement for the bioactivation of enalapril and hence its therapeutic effect. Pentopril is another ethyl ester prodrug of an angiotensin converting enzyme inhibitor which is highly stable in human plasma. Less than 50% of the oral dose of the prodrug ester appears to be hydrolyzed in vivo to the active parent acid (Tipnis, V. and Rakhit A., *J. Chromatog.* 345, 396, 1985).

Ester derivatives are generally enzymatically cleaved in vivo to release the bioactive parent drug. This may result in a large variation in drug bioavailability, as a function of the variability in enzymatic activity among individuals, or even in the same individual at various times during the day or in various sites where the drug is administered.

It has frequently been found to be desirable to prolong the action of a single dose of some drugs, for example, to prolong the period of activity while the patient is sleeping and to decrease the cost and effort of providing more frequent dosages. In the case of herbicides or pesticides, the longer the agent is available on the site of action the more effective it is. The carboxylic acid forms of these agents are in general hydrophilic and washed out from the site of action shortly after application by rain or irrigation. An hydrophobic water insoluble derivative which degrades slowly to release the active acid form for an extended period of time would increase the efficiency and effectiveness of these compounds.

It is therefore an object of the present invention to provide novel prodrugs characterized by a high susceptibility to undergo hydrolytic degradation and at the same time susceptible to variations in water and lipid solubilities of the derivatives.

It is another object of the present invention to provide prodrugs of compounds having carboxylic acid moieties that slowly degrade by hydrolysis in a designed, predictable and controlled fashion, to a form having the bio-affecting/pharmacological response characteristic of the acids from which they are derived, yet which are characterized in being less irritating to topical and gastric or intestinal mucosal membranes.

It is still another object to the present invention to provide prodrugs of carboxylic acid agents which are more capable of passage through biomembranes so that bioavailability is increased, especially when administered to the gastro-intestinal tract, the rectum, the blood brain barrier, the skin or the eye.

It is a further object of the present invention to provide derivatives of conventional carboxylic acids which are cleaved to release the original drug, while the remaining cleaved moiety is non-toxic and/or is metabolized to non-toxic derivatives.

It is still a further object of the present invention to provide derivatives of bioactive agents for general use such as herbicides, insecticides, fungicides, antimicrobials, pesticides, pheromones, and fertilizers that are more stable and hydrolyze to release the active agent in a controlled manner over an extended period of time, at the site or environment of application.

SUMMARY OF THE INVENTION

Compositions degrading by hydrolysis to release a bioactive compound having carboxylic acid moieties, which are organic acid anhydrides having the following formula:

Formula 1:

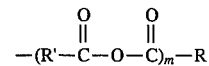

wherein R' is a residue of a therapeutic bioactive compound, for example, a non-steroidal anti-inflammatory agent such as naproxen, ibuprofen, indomethacin, or voltaren; a penicillin or cephalosporin antibiotic such as ampicillin or cefmetazole; or bioactive compounds for non-therapeutic use, for example, herbicides, insecticides, fungicides, antimicrobials, pesticides, pheromones, and fertilizers;

m is an integer of between 1 and 3; and

R is $C_{1-24}$ aklyl; $C_{2-24}$ alkenyl; phenyl; $C_{5-6}$ cycloalkyl; $C_{2-8}$ cycloalkenyl; aryl $C_{1-6}$ alkyl; $C_{1-6}$ alkyl-aryl; $(CH_2-CH_2-O)n$, where n is between 1 and 50; $(CH_2CHCH_3O)n$, where n is between1 and 50; aromatic or aliphatic anhydride oligomer of Mn<3,000; lactic and glycolic oligomers of Mn<3,000; caprolactone oligomers of Mn<3,000; natural and synthetic amino acids and derivatives thereof; oligopeptides;

mono or oligosaccharides; heterocyclic compounds, including nicotinic acid derivatives, and substituted derivatives thereof, including hydroxy, carboxy, and halogen derivatives. The resulting mixed anhydrides are characterized by having between one and three drug molecules attached to a single carrier molecule.

The prodrugs are highly susceptibility to hydrolytic degradation in a predictable and controlled fashion, have variable solubilities in water and lipids, with increased biomembrane transport, elicit a bioaffecting/pharmacological response, and are less irritating to topical and gastric or intestinal mucosal membranes.

DETAILED DESCRIPTION OF THE INVENTION

The present invention relates to novel and useful derivatives of biologically active agents containing a carboxylic acid function. In particular, the present invention relates to novel forms of compounds for use as drugs in humans and animals, and as agricultural bioactive agents:, including herbicides, insecticides, fertilizers, and insect pheromones. The compounds have several advantages over the compounds from they are derived: (1) they are released in a controlled manner for predicatable prolonged periods of activity; (2) they are more readily bioavailable; (3) they are less irritating to topical and gastric mucosal membranes; (4) they have an improved flavor, thereby reducing complaints by patients about the unpleasant bitter taste of carboxylic acid drugs; (5) they have different physical and chemical properties for formulation purposes and greater stability; and (6) they pass through topical membranes such as the surface of the eye or skin, or through the blood brain barrier, when administered orally, parenterally, or topically to animals.

The term "bioactive compound" refers to any compounds exerting a biological effect, including drugs for human and animal use, or agents for agricultural and household use, such as insecticides and herbicides. The term "prodrug" denotes a derivative of any bioactive compound having a carboxylic function, for example, naproxen, aspirin, 1-naphthylacetic acid, enalaprilate, or any of a number of pesticides, which derivative, that, when administered to a site of action, is cleaved by hydrolysis and/or enzymatic action in such a manner as to release the bioactive agent at its target site or sites of activity, with the remaining residues being non-toxic or metabolized to non-toxic compounds.

The compounds of the present invention are organic anhydrides having the following formula:

Formula 1:

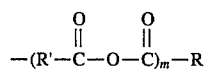

wherein R' is a residue of a therapeutic bioactive compound, for example, a non-steroidal anti-inflammatory agent such as naproxen, ibuprofen, indomethacin, or voltaren; a penicillin or cephalosporin antibiotic such as ampicillin or cefmetazole; or bioactive compounds for non-therapeutic use, for example, herbicides, insecticides, fungicides, antimicrobials, pesticides, pheromones, and fertilizers;

m is an integer of between 1 and 3; and

R is $C_{1-24}$ aklyl, $C_{2-24}$ alkenyl; phenyl; $C_{5-6}$ cycloalkyl; $C_{2-8}$ cycloalkenyl; aryl $C_{1-6}$ alkyl; $C_{1-6}$ alkyl-aryl; $(CH_2-CH_2-O)n$, where n is between 1 and 50; $(CH_2CHCH_3O)n$, where n is between 1 and 50; aromatic or aliphatic anhydride oligomer of Mn<3,000; lactic and glycolic oligomers of Mn<3,000; caprolactone oligomers of Mn<3,000; natural and synthetic amino acids and derivatives thereof; oligopeptides; mono or oligosaccharides; heterocyclic compounds, including nicotinic acid derivatives, and substituted derivatives thereof, including hydroxy, carboxy, and halogen derivatives. The resulting mixed anhydrides are characterized by having between one and three drug molecules attached to a single carrier molecule.

The free carboxylic acid drug is conjugated to an inert carrier or another drug via an hydrolytically lablie anhydride bond in order to alter the properties of the parent drug. Although little has been studied on the synthesis of, and release of compounds by hydrolytic cleavage in vivo, of bioactive drugs, biodegradable polymers based on these bonds have been developed and used as erodible carriers for drugs both in animals and humans. Unlike the ester bond discussed above, the anhydride bond is more susceptible to hydrolysis and the compound decomposes to its carboxylic acid counterpart at a predictable rate and pattern. The anhydride bond is much less sensitive to enzymolysis than esters or amides. Recent studies on polyanhydrides as drug carriers show that the anhydrides degrade in a controlled fashion and are biocompatible with the human body tissues, including the brain. See, for example, Leong, K. W., et al., *J. Biomed. Mat Res.* 20, 51, (1986); Laurencin, C., et al., *Proceed. Intern. Symp. Control. Rel. Bio. Mat.*, 14, 140,( 1987); Brem H. Ahn, H., 1988 *Annual meeting of the American Association of Neurological Surgeons*, pp. 349, and pp. 381.

The prodrug properties depend on the selected carrier. Mixed anhydrides of lipophilic fatty acid conjugate carriers, particularly oleic acid, (which are known as transdermal enhancers) can improve skin penetration. After the drug crosses the lipophilic stratum corneum layer to the viable epidermis, the fatty acid is split off by hydrolysis to leave the hydrophilic drug which can then be absorbed via the viable epidermis and dermis to the lymph and blood. Changing the physical form of the drug to a liquid at body temperature, or increasing the solubility via an ointment or creme base may also improve penetration through the skin. The duration of drug release can be designed by using carriers of increased hydrophobicity such as fatty acids of $C_{1-24}$ where increasing from 1 to 24 methylenes increases the hydrophobicity of the prodrug and slows its hydrolysis and the release of the active parent drug. In constrast, selection of an hydrophilic carrier such as polypropylene or ethylene glycol, or an oligosaccharide, can be used to produce a more hydrophilic substance.

Mixed anhydride prodrugs are particularly suitable for oral pharmaceutical formulations, since the anhydride bonds are more stable in acidic medium, and undergos minimal hydrolysis in the acidic pH of the stomach, but degrade and releases the drug at the neutral or basic pH of the intestine.

Carboxylic mixed anhydride prodrugs can be designed to cross the blood brain barrier using the dihydropyridine <=> pyridinium salt redox system (Bodor, N.; et al., *Science* 214, 1370 (1981); Pop, E.; *Pharm. Sci.*, 78, 609 (1989)). The carboxylic acid drug forms a mixed anhydride with nicotinic acid and then quarternizes to the trigonellinate (D-Q+). Alternatively, N-alkylnicotinic acids are reacted with the drug. The pyridinium salts are reduced to give the corresponding dihydropyridine drug delivery system. After systemic administration of this prodrug, it should partition into the brain as well as other peripheral compartments. For optimal activity the prodrug is expected to be oxidized to D-Q+ in the CNS as well as in the periphery. This will result in lower peripheral levels, but in the CNS, D-Q+ as a polar species is trapped within the blood brain barrier. In the CNS, D-Q+ will hydrolyze slowly to release the parent drug. This approach is suitable for brain-specific delivery of carboxylic acid drugs, such as dopa, hydantoinacetic acid, valproic acid, and various steroids.

The compounds of the present invention are conveniently administered to human of animals via conventional injectable, implantable, oral or topical administration. Such pharmaceutical compositions include tablets, solutions, suspensions, capsules, gels, suppositories, aerosol containers with inert carrier gases, such as fluorohydrocarbons, nitrogen, and air. These formulations are known to one skilled in the art, however further information can be found in "Remington's Pharmaceutical Science", A. R. Gennaro Editor, 17th Edition, 1985, Mack Publishing Company, Easton, Pa. Because these prodrugs hydrolyze in aqueous mediums, water must not be added to the formulation until immediately before use. An important consideration when selecting the conjugated carrier is the use of application. For prodrugs to be injected or implanted into the body, the biocompatibility, the toxicity, and elimination process of the conjugated carrier is of major concern. On the other hand, for pesticide or herbicide prodrug applications the toxicity or the product purity is less of a concern, as long as the requirements of the EPA are complied with.

Methods for the synthesis of anhydrides are well known. See, for example, *The Chemistry of Acid Derivatives, S. Patai ed. pt. 1*, (Wiley, New York 1979); and *Basic Principles of Organic Chemistry*, J. D. Roberts and M. C. Caserio editors, (W. A. Benjamin, California, 1965). Anhydrides can be formed from two carboxylic acid molecules using a dehydrative agent. Common dehydrating agents are acetic anhydride, phosgene, diphosgene, dicyclohexylcarbodiimide, and methoxyacetylene. However, since these methods result in the formation of symmetric anhydrides in addition to the desired mixed anhydrides, this method is not preferred for the preparation of highly pure mixed anhydrides. The preferred methods for the formation of mixed anhydrides of high purity without further isolation and purification is the reaction of an activated carboxylic acid derivative with a carboxylic acid or the salt thereof under mild conditions. The active acid derivative is Examples for mixed anhydride formation are:
1. R—COCl+R'—COOH→R—COOCO—R'
2. R—CH=C=O+R'—COOH→R—COOCO—R'
3. a. R—COOH+$C_6H_{11}$—N=C=N—$C_6H_{11}$→R—CO—C(NH—$C_6H_{11}$)=N—$C_6H_{11}$
   b. R—CO—C(NH—$C_6H_{11}$)=N—$C_6H_{11}$+R'—COOH→R—COOCO—R'+$C_6H_{11}$—NH—C—NH—$C_6H_{11}$
4. a. R—COOH+Cl—$SO_2$—N=C=O→R—COO—CO—NH—$SO_2$Sl
   b. R—COO—CO—NH—$SO_2$Cl—R'COOH→R—COOCO—R'

R and R' are either the drug or the conjugated carrier.

When preparing a mixed anhydride of a compound containing active functional groups in addition to the acid group, such as an hydroxyl or an amine, it is important to protect these groups so they will not interfere or interact during the anhydride formation process. The protecting group has to be removable without affecting the anhydride bond.

Such protecting groups can be selected from the protecting groups developed for the synthesis of peptides, especially those for the protection of amino acid side chains (Bodansky and Bodansky, *The Practice of Peptide Synthesis, Chapter IV pp* 119–157 (Elsiver, N.Y., 1985) and references thereof). Amino groups can be protected by inorganic or organic acid salts, or by a benzyloxycarbonyl, tert-butyloxycarbonyl, adamantyloxycarbonyl, and p-toluenesulfonyl protecting groups. Hydroxyl groups can be protected by carbonic acid derivatives, ethyloxycarbonyl and dibenzyloxycarbonyl groups, which can be removed by hydrogenolysis or by hydrolysis under mild conditions, with minimal effect on the anhydride bond.

The bioactive compounds must have at least one carboxylic acid available for anhydride formation. Examples of suitable compounds are described, for example, in *The Merck Index*, 11th edition, (Merck & Co., Inc. New Jersey, 1989). Preferred compounds include those derived from the following compounds:

Non-steroidal anti-inflammatory agents such as acetylsalicylic acid (aspirin); Salicylic acid; Sulindac; Indomethacin; Naproxene Voltaren; Fenoprofen; Ibuprofen; Ketoprofen; Diflunisal; Tolmetin; Flurbiprofen; Mefenamic acid; Suprofen; and Tolfenamic acid.

Cephalosporin antibiotics such as Cefametazole; Cefazolin; Cephalexin; Cefaclor; Cefuroxime; Cefamadole, and Cefoxitin.

Penicillin antibiotics such as Benzylpenicillin; Phenoxymethylpenicillin; Ampicillin; Carbenicillin; Azlocillin; and Piperacillin.

Steroidal monocarboxylic acids like: 6α-Fluoro-11β-hydroxy-16α-methyl-3,20-dioxopregna-1,4-dien-21-oic acid; 6α-Fluoro-11β,17α-dihydroxy-16β-methyl-3,20-dioxopregna-1,4-dien-21-oic acid; and 6α-Fluoro-11β,17α-dihydroxy-16β-methyl-3,20-dioxopregna-1,4-dien-21-oic acid.

Prostaglandins such as Prostaglandin E2; Prostaglandin E1; Prostaglandin F2β; Prostacylin; Ambaprostil; Nileprost; and Ciprostene.

Angiotensin-converting enzyme inhibitors such as Enalaprilic acid; Captopril; N-Cyclopentyl-N-[3-[(2,2-dimethyl-1-oxopropyl)thio]-2-methyl-1-oxopropyl]glycine; 1-[4-carboxy-2-2methyl-2R,4R-pentanoyl]- 2,3-dihydro-2S-indole-2-carboxylic acid; Lisinopril; Tiopronin; and Pivopril.

Various other bio-affecting carboxylic acid agents, such as Ethacrynic acid; Methyldopa; 5-Aminosalicilic acid; L-Dopa; Carbidopa; Valproic acid; 5-Hydantoinacetic acid; Tranexamic acid; Furosemide; Methotrexate; Chlorabucil; Clofibric acid; Amphotericin B; 6-Aminocaproic acid; Mecillinam; Tretioin; 4-Aminomethylbenzoic acid; Mycophenolic acid; D,L-2,4-Dihydroxyphenylalanione; All-trans-retinoic acid; 13-cis-retinoic acid; Folic acid; Cromoglycic acid; and Nicotinic acid.

Compounds used for control weeds and plants such as 2,4-dichlorophenoxy acetic acid (2,4-D); 2-methyl-4-chlorophenoxy acetic acid (MCPA); 2,4,5-trichlorophenoxypropionic acid (Silvaex); 2,4,5-trichlorophenoxyacetic acid (Z45-T) trichloroacetic acid (TCA); 2,2-dichloropropionic acid (Dalapon); N-(1-naphthyl)phthalamic acid (NPA; Naptalam; Alanap); 3,6-endoxohexahydrophthalic acid (Endothall); 1,2-dihydro-3,6-pyridazoinediione (Maleic Hydrazide, MH); and 2,3,6-trichlorobenzoic acid (2,3,6-TBA).

Disinfectants for general use such as 4-(dichlorosulphamoyl)benzoic acid (Halazone).

Particularly preferred mixed anhydride compounds of the invention, as described in formula 1, include those wherein R—COO is derived from one of the specific bioactive acids named above and the following conjugating carriers: saturated and unsaturated aliphatic acids including fatty acids; aliphatic and aromatic di- and tricarboxylic acids such as sebacic, adipic, isophthalic, benzenetricarboxylic acid, dimer and trimer fatty acids (Pripol® compounds available from Unichema); polyethylene and propylene glycols having carboxylic acid end groups; aliphatic and aromatic anhydride oligomers; nicotinic acid and derivatives thereof, another drug, and low molecular weight polymers based on lactic and glycolic acids.

The method and compositions of the present invention will be further understood with reference to the following non-limiting example.

EXAMPLE 1

Preparation of acetylsalicilic acid-stearic acid mixed anhydrides a. Acetylsalicoyl chloride (10 mmol) was dissolved in 5 ml toluene and pyridine (15 mmol) was added to produce a white precipitate of the acid chloride-pyridine adduct. To the stirred mixture a solution of stearic acid in toluene (10 mmol in 10 ml) was added and the mixture allowed to react for 2 hours at room temperature. The white precipitate was isolated by filtration and the solution was extracted with cold 1 N HCl solution, and the organic phase was dried over anhydrous $MgSO_4$. The clear solution was evaporated to dryness to yield a white solid which was recrystallized from dry ether (65% yield) 'H-NMR ($CDCl_3$, ppm) 0.9(t,3H), 1.3(s,28H), 1.7(m,2H), 2.3(s,3H), 2.5(m,2H),7.2(m,1H), 7.4(m,1H), 7.7(m,1H), 8.1(m,1H).

Other acid acceptors such as triethylamine, morpholine, polymeric amines, or inorganic bases can be used in this procedure instead of pyridine.

b. Acetylsalicilic acid-stearic acid mixed anhydrides were similarly obtained from the reaction of acetylsalicylic acid and stearoyl chloride, where acetylsalicylic acid was first dissolved in the pyridine solution and reacted with 20% stearoyl chloride in toluene.

Chloroform, dichloromethane, and other aromatic hydrocarbons can be used as solvents in either method.

c. Acetylsalicylic acid-acetic acid and stearic acid-acetic acid mixed anhydrides were prepared by reacting acetylsalicylic acid or stearic acid with excess acetic anhydride or acetic anhydride-xylene mixtures for 30 min under reflex conditions. The acetic acid mixed anhydrides were isolated by evaporation to dryness of the acetic anhydride and recrystallization from diethyl ether-hexane mixture. The mixed anhydride of acetic acid was prepared from the reaction of the acid with acetyl chloride as described in example 1a. Equivalent amounts of acetylsalicylic acid and stearic acid-acetic acid mixed anhydrides were mixed and melt reacted at 100°–150° C. under vacuum (>0.1 mm Hg) for 60 minutes. The resulting product contains the symmetrical anhydrides in addition to the mixed anhydride. This method is simple and cost effective, useful for agricultural application i.e. for controlled release of pesticides and insecticides, were the symmetrical anhydrides are less of a concern.

EXAMPLE 2

Preparation of acetylsalicylic acid-acid mixed anhydride a. Preparation of acetylsalicylic acid-acetic acid mixed anhydride: The mixed anhydride was prepared by the melt or solution polymerization methods as described in Example 1c. The products were characterized as follows. MP 86°–88° C.; IR(cm–1) 2920, 2840, 1790, 1730, 1600; 'H-NMR ($CDCl_3$, ppm) 2.3(d,6H), 7.2(d,1H),7.4(t, 1H), 7.7(t,1H), 8.1(d,1H). Yield: 70%.

b. Preparation of acetylsalicylic acid-lauric acid mixed anhydride: The mixed anhydride was prepared by the solution methods as described in Example 1a. The products were characterized as follows: MP 65°–68° C.; IR(cm–1) 2920, 2840, 1790, 1730, 1600; 'H-NMR ($CDCl_3$, ppm) 0.9(t,3H), 1.3(s,16H), 1.7(m,2H), 2.3(s,3H), 2.5(m,2H),7.2(m,1H), 7.4(m,1H), 7.7(m,1H), 8.1(m,1H). Yield: 65%.

c. Preparation of acetylsalicylic acid-oleic acid mixed anhydride: The mixed anhydride was prepared by the solution methods as described in Example 1a. The products were characterized as follows: MP 81°–83° C.; IR(cm–1) 2920, 2840, 1790, 1730, 1600; 'H-NMR ($CDCl_3$, ppm) 0.9(t,3H), 1.3(d,12H), 1.7(m,12H), 2.0 (m,4H), 2.2(s,3H), 5.4(m,2H), 7.3(m,2H), 7.7(m,1H), 8.1(d,1H). Yield: 70%.

d. Preparation of acetylsalicylic acid-octanoic acid mixed anhydride: The mixed anhydride was prepared by the solution methods as described in Example 1a. The products were characterized as follows: IR(cm–1) 2920, 2840, 1790, 1730, 1600; 'H-NMR ($CDCl_3$, ppm) 0.9(t,3H), 1.3(s,10H), 1.7(m, 2H), 2.3(s,3H), 2.5(m,2H), 7.2(m,1H), 7.4(m,1H), 7.7(m, 1H), 8.1(m, 1H). Yield: 60%.

EXAMPLE 3

Preparation of acetylsalicilic acid-dicarboxylic acid mixed anhydrides a. Mixed anhydride with sebacic acid: Sebacoyl chloride (10 mmol) was reacted with acetylsalicylic acid (20 mmol) in dichloromethane solution as described in Example 1a. Alternatively, Sebacic acid was reacted with acetylsalicoyl chloride as described in Example 1a. The products were characterized as follows: MP 65°–68° C.; IR($cm^{-1}$) 2920, 2840, 1810, 1740, 1600; 'H-NMR ($CDCl_3$, ppm)1.3(s,8H), 1.7(m,4H), 2.3(s,6H), 2.5(m,4H), 7.2(m,2H), 7.4(m,2H), 7.7(m,2H), 8.1(m,2H). Yield 70%.

b. Mixed anhydride with isophthalic acid: isophthaloyl chloride (10 mmol) was reacted with acetylsalicylic acid (20 mmol) in dichloromethane solution as described in Example 1a. Alternatively, isophthalic acid was reacted with acetylsalicoyl chloride as described in Example 1a. The products were characterized as follows: IR($cm^{-1}$) 2920, 2840, 1780, 1730, 1600; 'H-NMR ($CDCl_3$, ppm) 2.3(s,6H), 7.2(m,3H), 7.4(m,2H), 7.7(m,2H), 8.1(m,4H), 8.3(m,1H). Yield: 50%.

c. Mixed anhydride with adipic acid: adipoyl chloride (10 mmol) was reacted with acetylsalicylic acid (20 mmol) in dichloromethane solution as described in Example 1a. The products were characterized as follows: MP 56°–58° C.; IR($cm^{-1}$) 2920, 2840, 1810, 1740, 1600; 'H-NMR ($CDCl_3$, ppm) 1.7(m,4H), 2.3(s,6H), 2.5(m,4H), 7.2(m,2H), 7.4(m, 2H), 7.7(m,2H), 8.1(m,2H). Yield: 70%.

EXAMPLE 4

Preparation of anhydride oligomers with acetylsalicylic anhydride end groups

Acetylsalicylic acid-acetic acid mixed anhydride (10 mmol) were melt reacted with sebacic acid or adipic-acetic acid mixed anhydride (20, 50 and 200 mmol) at 150° C. under vacuum of 0.1 mm Hg for 30 minutes. Flexible materials which form a film from solvent were obtained. The data analysis is as follows:

TABLE I

| Analysis of anhydride oligomers with acetylsalicilic anhydride end groups. | | | | |
|---|---|---|---|---|
| Monomer ratio | | Melting | Molecular weight | |
| mmol/mmol | | point (°C.) | Mw | Mn |
| Sebacic Acid | 1:2 | 54–57 | 760 | 520 |
|  | 1:5 | 62–65 | 1150 | 910 |
|  | 1:20 | 63–66 | 2900 | 1910 |
| Adipic Acid | 1:2 | 45–49 | 340 | 310 |
|  | 1:5 | 46–49 | 810 | 530 |

TABLE I-continued

Analysis of anhydride oligomers with acetylsalicilic anhydride end groups.

| Monomer ratio mmol/mmol | Melting point (°C.) | Molecular weight Mw | Mn |
|---|---|---|---|
| 1:20 | 52–57 | 1680 | 1100 |

The oligomers had similar 'H-NMR spectra to the samples of Examples 3a and 3c with an increase in the sebacic and adipic acids peak integrations according to their content. IR was identical in all, with sharp peaks at 2920, 2840, 1800, 1740, and 1600 cm−1. Yield: >90%.

EXAMPLE 5

Preparation of naphthylacetic acid-aliphatic acid mixed anhydrides

The mixed anhydrides with stearic, lauric, octanoic, and acetic acid were prepared in dichloromethane using the same procedure described in Example 1. Naphthylacetic acid-stearic acid mixed anhydrides. The products were characterized as follows: MP 70°–75° C.; IR(cm$^{-1}$) 3040, 2920, 2840, 1800, 1730, 1600; 'H-NMR (CDCl$_3$, ppm) 0.9(t,3H), 1.3(s,28H), 1.7(m,2H), 2.4(m,2H), 4.1(d,2H), 7.3–8.0(m, 7H). Yield: 70%. Naphthylacetic acid-lauric acid mixed anhydrides, MP 102°–106° C.; IR(cm$^{-1}$) 3040, 2920, 2840, 1800, 1730, 1600; 'H-NMR (CDCl$_3$, ppm) 0.9(t,3H), 1.3(s, 16H), 1.7(m,2H), 2.4(m,2H), 4.1(d,2H), 7.3–8.0(m,7H). Yield: 75%. Naphthylacetic acid-acetic acid mixed anhydrides, MP 112°–116° C.; IR(cm−1) 3040, 2920, 2840, 1800, 1730, 1600; 'H-NMR (CDCl$_3$, ppm) 2.3(s,3H), 4.1(d, 2H), 7.3–8.0(m,7H).

EXAMPLE 6

Preparation of benzoic acid-aliphatic acid mixed anhydrides

The mixed anhydrides with stearic, lauric, octanoic, and acetic acid were prepared in dichloromethane using the same procedure described in Example 1.

Benzoic acid-stearic acid mixed anhydrides. The products were characterized as follows: MP 68°–72° C.; IR(cm−1) 2920, 2840, 1800, 1730, 1600; 'H-NMR (CDCl$_3$, ppm) 0.9(t,3H), 1.3(s,28H), 1.7(m,2H), 2.5(m,2H), 7.6(m,3H), 8.1(m,2H). Yield: 65%. Benzoic acid-lauric acid mixed anhydrides, MP 74°–76° C.; IR(cm−1) 2920, 2840, 1800, 1730, 1600; 'H-NMR (CDCl$_3$, ppm) 0.9(t,3H), 1.3(s,16H), 1.7(m,2H), 2.5(m,2H), 7.6(m,3H), 8.1 (m,2H). Yield 70%.

EXAMPLE 7

Preparation of nicotinic acid-aliphatic acid mixed anhydrides

The mixed anhydrides with indomethacin and ibuprofen were prepared from the reaction of indomethacin or ibuprofen with nicotinoyl chloride-HCl in pyridine-dichloromethane solution using the same procedure as described in Example 1. Ibuprofen-nicotinic acid mixed anhydride was isolated as a clear liquid which slowly crystallized after a few days to clear crystals having a low melting point, yield 75%. The Ibruprofen product was characterized as follows: IR(film cast, cm−1) 2960 (broad), 1810, 1740, 1700, (sharp). 'H-NMR (CDCl$_3$, ppm) 0.9 (d,6H), 1.5(d,3H), 1.8(p, 1 H) 2.2(d,2H), 3.8(q, 1H), 7.0–7.9(m,8H).

Indomethacin-nicotinic acid mixed anhydride was isolated as a slightly yellow solid with a yield of 52%. MP 82.4° C.; IR(film cast, cm−1) 2960 (broad), 1810, 1740, 1700, (sharp). 'H-NMR (CDCl$_3$, ppm) 2.2(s,3H), 3.8(s,2H), 3.9(s, 3H), 6.6, 8.0 (m,11H).

These nicotinic acid mixed anhydrides can be converted to the corresponding dihydrotrigonellinate brain delivery systems by quarternization with methyl iodide followed by reduction. Alternatively, the dihydropiridinium mixed anhydride derivative can be prepared from the direct reaction of the reduced nicotinic acid derivative and the acid drug. This example demonstrates the formation of mixed anhydride of an acid containing an amine group and as a carrier for brain specific delivery.

EXAMPLE 8

Preparation of acetylsalicilic acid-polyethyleneglycol mixed anhydride

Polyethyleneglycol monomethyl ether (MW-600) was reacted with succinic anhydride in refluxing tetrahydrofuran containing a catalytic amount of p-toluenesulfonic acid. The polyethyleneglycol monomethyl ether succinate derivative was isolated by precipitation in water-methanol mixture. The dried polymer was reacted with an equivalent amount of acetylsalicoyl chloride as described in example 1. The product was a white semisolid, IR(cm−1) 2920, 2840, 1800, 1730, 1600. 'H-NMR (CDCl$_3$, ppm) 1.7(m,2H), 1.9(m,2H), 2.2(s,3H), 3.7(s,49H), 7.3(m,2H), 7.7(m,1H), 8.1(d,1H).

EXAMPLE 9

Preparation of lauric acid mixed anhydrides of various drugs

The mixed anhydrides of indomethacin, ibuprofen, voltaren (diclofenac), mefenamic acid, and naproxen, were prepared in dichloromethane using the same procedure described in example 1.

The yield was 50 to 75% and the data analysis is shown in Table II:

TABLE II

Characteristics of lauric acid mixed anhydrides of drugs.

| Drug | IR(cm$^{-1}$) | 'H-NMR(CDCl$_3$, ppm) | Appearance |
|---|---|---|---|
| indomethacin | 2920, 2840, 1800, 1740, 1680, 1590 | 0.9(t,3),1.3(s,16),1.7(m,2) 2.2(s,3),2.5(m,2),3.8(d,6), 6.6–7.7(m,7) | yellow solid |
| ibuprofen | 2920, 2840, 1810, 1740, 1710, 1510 | 0.9(t,9),1.3(s,16),1.5(d,3) 1.7(m,2),1.9(p,1),2.2(m,5), 2.4(m,2),3.7(q,1),7.1(q,4) | clear liquid |
| voltaren | 2920, 2840, 1820, | 0.9(t,3),1.3(s,16),1.7(m,2) | white |

TABLE II-continued

Characteristics of lauric acid mixed anhydrides of drugs.

| Drug | IR(cm⁻¹) | ¹H-NMR(CDCl₃, ppm) | Appearance |
|---|---|---|---|
| | 1740, 1710, 1610 | 2.3(t,2),2.4(t,1),6.4(d,1), 7.0–7.7(m,7) | solid |
| mefenamic acid | 3320, 2920, 2840, 1800, 720, 1690, 1690, 1600 | 0.9(t,3),1.3(s,16),1.7(m,3) 2.2(m,9),6.6–7.5(m,8) | yellow solid |
| naproxen | 2920, 2840, 1810 1740, 1700, 1600 | 0.9(t,3),1.3(s,16),1.7(m,3), 2.4(m,2),3.9(m,4),7–7.7(m,6) | white solid |
| valproic acid | 2920, 2840, 1810, 1740 | 0.9(t,9),1.3(s,20),1.7(m,2), 1.8(m,4),2.5(m,2),2.7(m,1) | clear liquid |

EXAMPLE 10

Preparation of Drug-acetylsalicilic acid mixed anhydride a. Preparation of indomethacin-acetylsalicilic acid mixed anhydride: Indomethacin (10 mmol) was reacted with acetylsalicoyl chloride in pyridine:dichloromethane solution, at room temperature for 1 hour. The mixed anhydride was isolated as described in example 1, to yield a white powder (70% yield) which melted at 162°–164° C. IR (nujol, cm⁻¹) 1800, 1740, 1670, 1600 (all sharp single peaks).

b. Preparation of ibuprofen-acetylsalicilic acid mixed anhydride:

Ibuprofon (10 mmol) was reacted with acetylsalicoyl chloride in pyridine:dichloromethane solution, at room temperature for 1 hour. The mixed anhydride was isolated as described in example 1, to yield a clear liquid which slowly crystallized after few days to yield clear crystals with low melting points (70% yield). IR (film cast, cm⁻¹) 2960 (broad), 1800 (broad), 1740, 1600 (sharp). ¹H-NMR (CDCl₃, ppm).

EXAMPLE 11

Hydrolytic degradation

Compressed tablets (10,000 psi, 200 mg, 1.4 cm diameter) of various anhydride derivatives of drugs were placed in 200 ml phosphate buffer solution pH 7.4 at 37° C. The solution was replaced periodically with fresh buffer solution and the concentration of drug released to the solution was determined by UV spectrophotometer at 230, 254, and 280 nm. The results are shown in Table III and IV as follows:

TABLE III

Hydrolytic Degradation of Acetylsalicylic Mixed Anhydrides

| Mixed anhydride | Degradation (%) at: | | | | | |
|---|---|---|---|---|---|---|
| | 4 | 24 | 48 | 72 | 120 | 200 hours |
| Aspirin (ASP) | 100 | | | | | |
| ASP-acetate | 38 | 64 | 85 | 96 | 100 | |
| ASP-laurate | 5 | 22 | 33 | 40 | 63 | 70 |
| ASP-oleate | 3 | 9 | 15 | 20 | 32 | 42 |
| ASP-stearate | 8 | 15 | 25 | 34 | 50 | 68 |
| ASP-benzoate | 25 | 41 | 65 | 93 | 100 | |
| ASP-adipate oligomer Mn = 950 | 2 | 25 | 43 | 67 | 98 | 100 |
| ASP-Indomethacin | 0 | 4 | 9 | 15 | 31 | 45 |
| diASP-sebacate | 2 | 5 | 31 | 75 | 92 | 100 |
| ASP-sebacate oligomer Mn = 1120 | 1 | 20 | 53 | 76 | 88 | 100 |

When tablets of ASP-stearate, acetate or laurate and NAP-stearate mixed anhydrides were placed in pH 1.2 solution at 37° C., no drug release was detected for 24 hours and less than 5% was detected after 72 hours.

TABLE IV

Degradation of Various Mixed Anhydrides

| Mixed anhydride | Degradation (%) | | | | | |
|---|---|---|---|---|---|---|
| | 4 | 24 | 48 | 72 | 120 | 200 hours |
| Indomethacin (IND) | 75 | 100 | | | | |
| Mefenamic acid (MFN) | 66 | 100 | | | | |
| 1-Naphthalene acetic acid (NAP) | 45 | 78 | 100 | | | |
| Bezoic acid (BNZ) | 100 | | | | | |
| IND-stearate | 6 | 17 | 28 | 36 | 51 | 70 |
| NAP-stearate | 0.4 | 1.2 | 4 | 5.8 | 10 | 17 |
| NAP-sebacate (oligomer Mn = 720) | 2.3 | 27 | 53 | 68 | 78 | 82 |
| MFN-stearate | 4 | 24 | 33 | 42 | 64 | 71 |
| BZN-stearate | 6 | 13 | 22 | 28 | 39 | 48 |

EXAMPLE 12

Anti-inflammatory Effect of Mixed Anhydride Prodrugs of Indomethacin, Ibuprofen, and Aspirin The acetate and stearate mix anhydrides of acetylsalicilic acid, indomethacin and ibuprofen were tested for their antiinflammatory activity using a Nsaid Rat Paw Edema model. 50 mg equivalents of acetylsalicylic acid and ibuprofen, and 10 mg equivalents of indomethacin of the stearate and acetate mixed anhydrides (<100 micron particle size) were suspended in 1.0 ml of sterile water. Water solutions of the original acid drugs were used as reference. The protocol was as follows: Sprague-Dawley rats averaging 300 gm in weight (6 in each group) were injected with 100 microliter of drug suspension into the foot at the same time as carrageenan was injected. The activity of the drug was determined by the effect of drug on the edema or swelling of the foot, the lower the volume compare to the carrageenan controls, the more effective the drug. Edema was measured with a plethysmometer. The results are summarized in table V.

TABLE V

Antiinflammatory Effect of Mixed Anhydride Prodrugs of Indomethacin, Ibuprofen, and Aspirin on Carrageenan Edema in Rats.

| Formulation | Edema, ml | | | |
|---|---|---|---|---|
| | 6 hr | 24 hr | 48 hr | 72 hr |
| Carrageenan-control | 0.94 | 0.75 | 1.07 | 0.92 |
| Aspirin (AS) | 0.76 | 0.85 | 0.90 | 0.98 |
| ASP-acetate anhydride | 0.42 | 0.50 | 0.93 | 0.96 |
| ASP-stearate anhydride | 0.48 | 0.50 | 0.42 | 0.35 |
| Ibuprofen (IBU) | 0.65 | 0.92 | 0.95 | 1.06 |
| IBU-acetate anhydride | 0.35 | 0.48 | 0.83 | 0.95 |
| IBU-stearate anhydride | 0.45 | 0.58 | 0.42 | 0.45 |
| Indomethacin (IND) | 0.78 | 0.95 | 0.89 | 0.94 |
| IND-acetate anhydride | 0.30 | 0.40 | 0.63 | 0.95 |
| IND-stearate anhydride | 0.35 | 0.38 | 0.42 | 0.55 | n = 5 animals per point, p < 0.005.

All stearate formulations were active for more than three days. All of the acetate formulations were active for about 24 hours. The reference indomethacin, acetylsalicylic acid, and ibuprofen solutions were active for less than six hours. This data demonstrate the effectiveness of the prodrugs for controlled delivery of drugs.

Modifications and variations of the compositions, and methods of preparation and use thereof, of the present invention will be obvious to those skilled in the art from the foregoing detailed description of the invention. Such modifications and variations are intended to come within the scope of the appended claims.

I claim:

1. A mixed anhydride having the formula

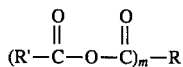

wherein R is selected from the group consisting of $C_{2-24}$ alkenyl; $C_{5-6}$ cycloalkyl; $C_{2-8}$ cycloalkenyl; aryl $C_{1-6}$ alkyl; $C_{1-6}$alkyl-aryl; $CH_3(CH_2-CH_2-O)n$, where n is between 1 and 50; $CH_3(CH_2CHCH_3O)n$, where n is between 1 and 50; lactic and glycolic oligomers of Mn<3,000; caprolactone oligomers of Mn<3,000; amino acids; peptides; saccharides; and heterocyclic compounds, selected from the group consisting of nicotinic acid, and hydroxy, carboxy and halogen substituted nicotinic acids;

R' is derived from a compound selected from the group consisting of acetylsalicylic acid; salicylic acid; indomethacin; sulindac; naproxen; fenoprofen; ibuprofen, ketoprofen; diflunisal; tolmetin; flurbiprofen; mefenamic acid; suprofen; and tolfenamic acid;

m is an integer of between 1 and 3; and wherein R and R' are different.

2. A mixed anhydride having the formula

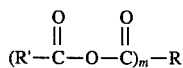

wherein R is derived from a compound selected from the group consisting of unsaturated aliphatic acids; aliphatic and aromatic di and tricarboxylic acids, dimer and trimer fatty acids; polyethylene and propylene glycols having carboxylic acid end groups; nicotinic acid; and low molecular weight polymers based on lactic and glycolic acid, R' is derived from a compound selected from the group consisting of acetylsalicylic acid; salicylic acid; indomethacin; sulindac; naproxin; fenoprofen; ibuprofen, ketoprofen; diflunisal; tolmetin; flurbiprofen; mefenamic acid; suprofen; and tolfenamic acid;

m is an integer of between 1 and 3; and wherein R and R' are different.

3. The mixed anhydride of claim 1 further comprising a pharmaceutically acceptable vehicle.

4. The mixed anhydride of claim 2 further comprising a pharmaceutically acceptable vehicle.

5. The mixed anhydride of claim 1, wherein R' is derived from indomethacin.

6. The anhydride of claim 2, wherein the compound R is derived from is selected from the group consisting of lauric acid, stearic acid, benzenetricarboxylic acid, oleic acid, sebacic acid, adipic acid, isophthalic acid, and nicotinic acid.

7. The anhydride of claim 2, wherein the compound R is derived from is a fatty acid.

8. A mixed anhydride having the formula

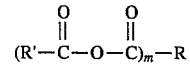

wherein R is derived from a compound selected from the group consisting of lauric acid, stearic acid, benzenetricarboxylic acid, oleic acid, sebacic acid, adipic acid, isophthalic acid, nicotinic acid, or R is selected from the group consisting of $C_{2-24}$ alkenyl; $C_{5-6}$ cycloalkyl; $C_{2-8}$ cycloalkenyl; aryl $C_{1-6}$alkyl; $C_{1-6}$alkyl-aryl; $CH_3(CH_2-CH_2-O)n$, where n is between 1 and 50; $CH_3(CH_2CHCH_3O)n$, where n is between 1 and 50; lactic and glycolic oligomers of Mn<3,000; caprolactone oligomers of Mn<3,000; amino acids peptides; saccharides; and heterocyclic compounds, selected from the group consisting of nicotinic acid, and hydroxy, carboxy and halogen substituted nicotinic acids, R' is selected from the group consisting of indomethacin, acetylsalicylic acid, and salicylic acid, m is an integer of between 1 and 3; and wherein R and R' are different.

9. A mixed anhydride having the formula

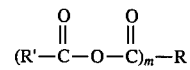

wherein R is derived from a compound selected from the group consisting of aliphatic and aromatic di and tricarboxylic acids, benzenetricarboxylic acid, dimer and trimer fatty acids; polyethylene and propylene glycols having carboxylic acid end groups; nicotinic acid; and low molecular weight polymers based on lactic and glycolic acid;

R' is selected from the group consisting of indomethacin, acetylsalicylic acid, and salicylic acid, m is an integer of between 1 and 3; and wherein R and R' are different.

10. The anhydride of claim 8, wherein R' is indomethacin.

11. The anhydride of claim 9, wherein R' is indomethacin.

* * * * *